United States Patent
Heuft

(10) Patent No.: US 9,867,890 B2
(45) Date of Patent: Jan. 16, 2018

(54) INSPECTION OF CONTAINERS

(71) Applicant: HEUFT SYSTEMTECHNIK GMBH, Burgbrohl (DE)

(72) Inventor: Bernhard Heuft, Burgbrohl (DE)

(73) Assignee: Heuft Systemtechnik GmbH, Burgbrohl (DE)

( * ) Notice: Subject to any disclaimer, the term of this patent is extended or adjusted under 35 U.S.C. 154(b) by 0 days.

(21) Appl. No.: 15/304,481

(22) PCT Filed: Apr. 17, 2015

(86) PCT No.: PCT/EP2015/058418
§ 371 (c)(1),
(2) Date: Oct. 14, 2016

(87) PCT Pub. No.: WO2015/158907
PCT Pub. Date: Oct. 22, 2015

(65) Prior Publication Data
US 2017/0035919 A1 Feb. 9, 2017

(30) Foreign Application Priority Data

Apr. 17, 2014 (DE) ........................ 10 2014 005 650

(51) Int. Cl.
*A61L 2/10* (2006.01)
*A61L 2/28* (2006.01)
(Continued)

(52) U.S. Cl.
CPC ........ *A61L 2/10* (2013.01); *A61L 2/28* (2013.01); *B08B 9/46* (2013.01); *G01N 21/64* (2013.01);
(Continued)

(58) Field of Classification Search
CPC .......... A61L 2/10; A61L 2/28; A61L 2202/14; B08B 9/46; G01N 21/64; G01N 21/9018; G01N 21/9072; G01N 21/909
See application file for complete search history.

(56) References Cited

U.S. PATENT DOCUMENTS 2,368,350 A 1/1945 Ellison
4,830,192 A 5/1989 Plester et al.
(Continued)

FOREIGN PATENT DOCUMENTS

DE 4223269 A1 1/1994
DE 102010043131 B4 10/2013
(Continued)

OTHER PUBLICATIONS

English translation of International Preliminary Report on Patentability issued in parent application PCT/EP2015/058418, dated Oct. 18, 2016, 6 pages.
(Continued)

*Primary Examiner* — Mark R Gaworecki
(74) *Attorney, Agent, or Firm* — Drinker Biddle & Reath LLP

(57) ABSTRACT

An apparatus for inspecting empty containers in order to detect dirt therein is disclosed. A radiation source generates exciting radiation, and the exciting radiation is directed onto the inner wall of a container and excites dirt to be detected in such a way that the dirt emits luminescent radiation. At least one device detects the luminescent radiation emitted by the dirt, and another device analyzes the detected luminescent radiation. Also disclosed is a corresponding method for inspecting empty containers in order to detect dirt therein.

20 Claims, 3 Drawing Sheets

(51) Int. Cl.
*B08B 9/46* (2006.01)
*G01N 21/90* (2006.01)
*G01N 21/64* (2006.01)

(52) U.S. Cl.
CPC ..... *G01N 21/9018* (2013.01); *G01N 21/9072* (2013.01); *A61L 2202/14* (2013.01); *G01N 21/909* (2013.01)

(56) References Cited

U.S. PATENT DOCUMENTS

| | | |
|---|---|---|
| 7,703,262 B2 | 4/2010 | Till |
| 8,368,747 B2 | 2/2013 | Brinz et al. |
| 2010/0288942 A1* | 11/2010 | Van Dijk ............... G01N 19/08 250/458.1 |

FOREIGN PATENT DOCUMENTS

| | | |
|---|---|---|
| EP | 1614630 A1 | 1/2006 |
| GB | 1182413 A | 2/1970 |
| JP | 2005265812 A | 9/2005 |
| WO | 89/09391 A1 | 10/1989 |
| WO | 2008/092537 A1 | 8/2008 |

OTHER PUBLICATIONS

Search report issued in parent application DE 102014005650.3, dated Apr. 29, 2014, 7 pages.

* cited by examiner

INSPECTION OF CONTAINERS

CROSS REFERENCE TO RELATED APPLICATIONS

This application is the National Stage Entry of PCT Application No. PCT/EP2015/058418 filed Apr. 17, 2015, which claims the priority benefit of German Patent Application No. 10 2014 005 650.3 filed Apr. 17, 2014, the contents of all being incorporated herein by reference.

BACKGROUND

Disclosed herein are a method and an apparatus for inspecting empty containers for contaminants, with a radiation source for generating an exciting radiation, wherein the exciting radiation is directed on to the inner wall of an empty container and there excites contaminants to be detected in such a way that they emit luminescent radiation, with at least one device for detecting the luminescent radiation emitted by the contaminants and with a device for analysing the detected luminescent radiation.

The present disclosure is intended in particular for use in automatic filling systems in which the containers are transported at high speeds of up to 90,000 bottles per hour. To avoid any negative effect on the throughput of such bottle filling systems, the inspection devices for monitoring the containers must also be designed to inspect the containers at high speeds.

In automatic filling systems, empty containers are examined for possible contaminants or foreign bodies before being filled. Conventionally, this involves passing the containers through an inspection device which comprises a light source for visible light and a CCD camera. This substantially involves shining light through the containers and inspecting them from various viewing angles so that a reliable detection of contaminants is ensured. Such an inspection device is known e.g. from EP 0 415 154 A1.

It has been shown that, with conventional inspection devices, certain contaminants, in particular organic contaminants such as mould fungi, fats, hydrocarbons, insect larvae, microbes or plastics, are very difficult or even impossible to detect with such inspection devices.

Furthermore, it is known that some, in particular organic, contaminants exhibit luminescence phenomena, i.e. that, by the action of energy from an external source, they can be shifted into excited states and can then return to the ground state by emitting luminescent radiation. The various types of luminescence are categorized here according to the duration of the glow after the excitation has ended. Fluorescence denotes a very brief afterglow occurring as a direct consequence of and a concomitant phenomenon to the excitation. The term phosphorescence describes a longer afterglow lasting longer than 1 ms after the excitation has ended.

The excitation generally takes place here by irradiation with UV light. UV light is not conventionally used for inspecting containers since container glass in particular has very low or even no transparency to UV light.

From WO 2008/092537 A1, an apparatus for the optical characterization of sample material is known, wherein inter alia UV light is employed. At least one UV detector is provided, with which the fluorescence or luminescence of the sample can be determined. Since the illumination of the sample takes place from outside through the container wall, this must be transparent to the radiation used.

From DE 10 2010 043 131 B1, an apparatus for the contactless investigation of a property of the contents of a container by means of electromagnetic radiation is known. The container can be for example a grain silo, a fermentation tank or a similar container and the apparatus is used to carry out a contactless measurement to monitor the progress of the process of the contents located in the container. Since the penetration depth of the radiation can be relatively low, a device is provided with which a medium is streamed into the container in order to create a vortex in the interior of the container. The medium causing the vortex in this case is transparent to electromagnetic radiation, so that in the interior of the vortex a contactless measurement can be performed to determine a property of the contents of the container.

SUMMARY

The object of the present disclosure is to increase the reliability of an inspection device for containers without significantly increasing the residence time of the container in the inspection device.

This object is achieved according to the disclosure by the fact that the inner walls of an empty container are illuminated by means of a radiation source and the luminescent radiation produced by contaminants adhering to the inner walls of the container is detected in a suitable device and then analysed. Since the material generally used for containers has low transparency to the exciting radiation, the illumination of the inner walls takes place via an opening, e.g. the mouth opening, of the empty container.

The radiation source is preferably an electromagnetic radiation source, e.g. a radiation source for light in the visible range, a UV-A, UV-B, UV-C or X-ray radiation source or a combination thereof.

It is known that UV-C radiation has a microbicidal action. By using UV-C radiation, therefore, it is additionally and advantageously possible to utilize the fact that light organic contamination by bacteria, spores or fungi can be not only detected but at the same time also destroyed, so that containers with such contaminants do not have to be rejected from the filling device.

The radiation source can be operated in pulsed mode and controlled such that the light pulses are emitted only when a container is located in front of the radiation source. Owing to the generally low transparency of the container material to the exciting radiation, the container itself acts as a radiation shield, so that only very little radiation, if any, reaches the outside. Additional shielding of the inspection apparatus can then be very simple in design or can even be omitted entirely. Pulsed operation has the further advantage that it results in a reduction of movement-related blurring in the detection devices.

The radiation source can also be a continuous radiation source which is employed in continuous operation. Fluorescent tubes or fluorescent lamps, for example, are particularly suitable.

The container wall of containers typically used in the drinks industry is not transparent to the exciting radiation, and so the exciting radiation or the radiation source itself has to be directed or introduced into the interior of the container through the container opening in order to irradiate the inner wall of the container.

The radiation source is preferably arranged outside the container and the exciting radiation is directed through the mouth opening into the interior of the container e.g. via one or more mirrors.

In a further embodiment, a device can be provided with which an apparatus head is introduced into the container through the mouth opening. On the apparatus head, for example an optical waveguide can be arranged, via which the exciting radiation is directed into the container. Alternatively, the apparatus head can also comprise the radiation source itself. The apparatus head can also comprise detection devices for detecting the reflected radiation.

The luminescent radiation emitted by the contaminants can be guided out of the container through the mouth opening of the container and for example be directed on to a detection device using a mirror. Such an arrangement has the advantage that it is particularly simply configured since only a single device is required for detecting the luminescent radiation.

Advantageously, the mirror is a dichroic mirror, which lets through the incident radiation to be directed into the container and reflects the luminescent radiation exiting from the mouth opening of the container, which has a higher wavelength than the exciting radiation, and directs it on to the detection device.

The part of the exciting radiation that is reflected back out of the container, on the other hand, is not deflected by the dichroic mirror and therefore does not strike the detection device. A radiation filter may optionally be additionally provided in front of the detection device for the selective blocking of UV radiation or of undesired radiation frequencies in general.

In a preferred embodiment, the luminescent radiation emitted by the contaminants is guided out of the container through the walls of the container and collected by one or more detection devices, which are arranged around the container. This embodiment is suitable if, owing to the geometry of the container, a direct Illumination of the inner wall of the container cannot be achieved via the mouth opening. It is a prerequisite for this, of course, that the container wall must be transparent to at least part of the expected luminescent radiation. Conventional container glass meets this prerequisite.

Both the arrangement and the number of the detection devices employed can be selected at will in this embodiment. It is crucial only that an image of the entire inner wall of the container is achieved in order to ensure that the entire container is inspected for contaminants.

Guiding the luminescent radiation out of the interior of the container via the container wall is also suitable in embodiments in which the radiation source is introduced into the container through the container mouth and thus the ray path of the luminescent radiation through the container opening is blocked.

The devices for detecting the luminescent radiation are preferably CCD cameras. To avoid or reduce movement-related blurring, shutter cameras with high shutter speeds can be employed. This is particularly advantageous if the radiation source is working in continuous operation. To increase the radiation intensity, the exciting radiation can be focused on to the mouth opening using a lens.

The disclosure also relates to a method for inspecting empty containers for contaminants. The method comprises the steps of irradiating the inner walls of the container with a radiation source, detecting the luminescent radiation emitted by any contaminants present using a detection device and analysing the detected luminescent radiation in an analysing device.

If a strong UV radiation source, e.g. a UV-C radiation source, is used in the method according to the disclosure, there is the advantage that not only can the radiation be used to detect the contaminants but at the same time contaminants such as microbes, bacteria, fungi or spores can also be destroyed by the radiation.

In detecting the contaminations, a high degree of sensitivity is also created which makes it possible e.g. to distinguish between weak but large-surface-area contaminations, such as microbial contamination, and coarser contaminants. Thin microbial layers can be destroyed by irradiation with UV-C radiation, so that it is then not necessary to reject such a container from the filling process. If, on the other hand, coarser contaminants are found in a container, this container must be cleaned again.

According to a further preferred embodiment, contaminated containers are rejected only if the detected luminescent radiation exceeds a previously set limit value. To identify and characterize the contaminations, the image of the container based on the luminescent radiation is fed into an electronic image analyser, which for example detects particularly light-coloured areas or colour differences. The analysis can take place for example by comparison with stored data or patterns. In the case of deviations or where a limit value is exceeded, the electronic analyser returns a fault signal which then leads to the rejection of the relevant container if appropriate.

The present disclosure is suitable for detecting both fluorescent and phosphorescent contaminants.

Embodiments can furthermore be employed for inspecting containers made of any material. Particularly advantageously, embodiments can be employed for containers made of materials that are non-transparent to the exciting radiation but transparent to the luminescent radiation. Embodiments are therefore particularly suitable for use with containers made of glass or transparent plastics, such as e.g. PET.

BRIEF DESCRIPTION OF THE DRAWINGS

With the aid of the following figures, the method and apparatus of the present disclosure are explained in more detail. There are shown in.

DETAILED DESCRIPTION

Figure 1:
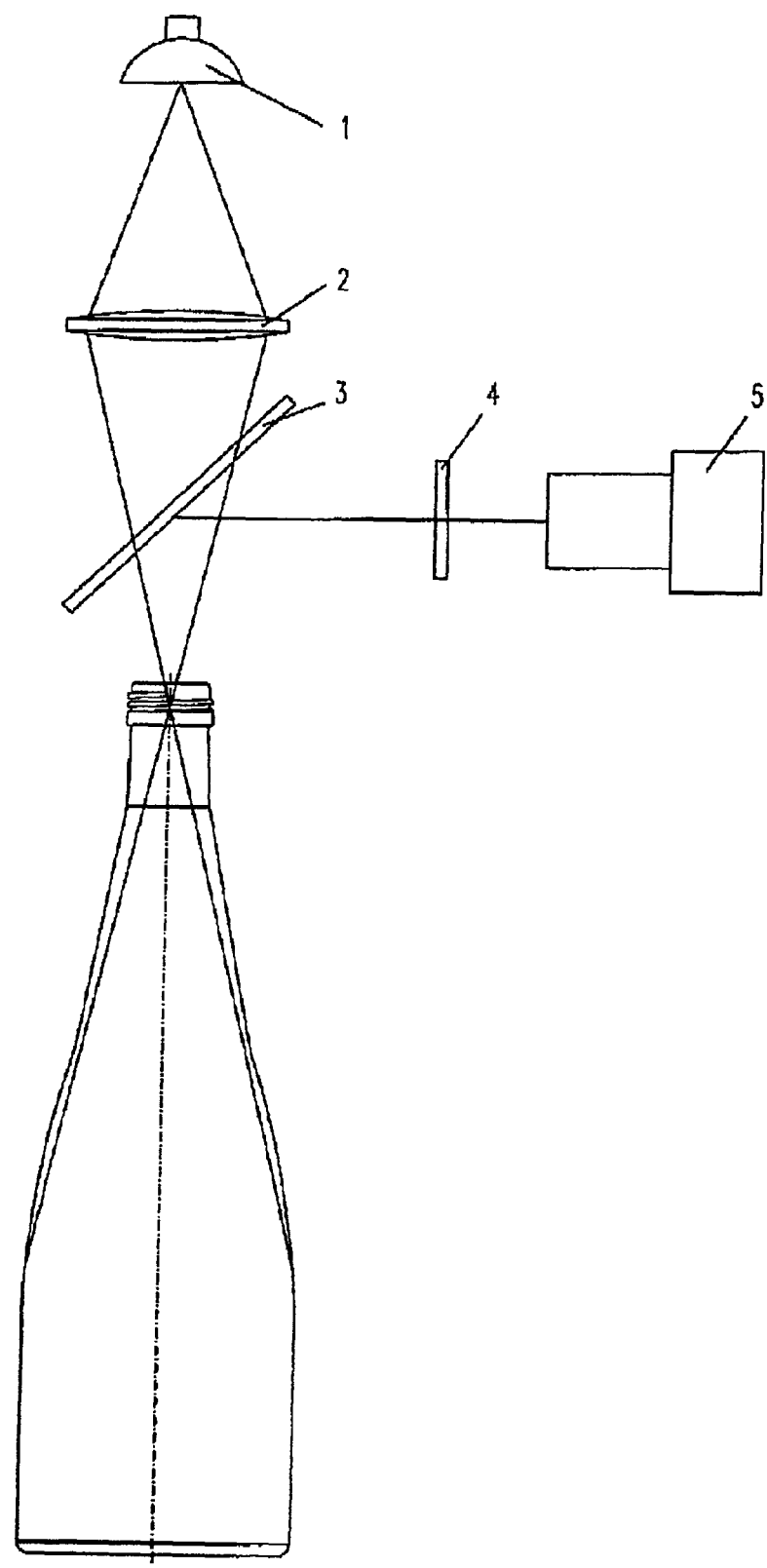
FIG. 1 a pictorial schematic of a first apparatus for inspecting empty containers.

The apparatus depicted in FIG. 1 comprises an electromagnetic radiation source 1, the radiation of which is focused using a lens 2 in the area of the mouth of a bottle. The radiation here passes through a dichroic mirror 3 arranged between the lens 2 and the bottle mouth. The dichroic mirror 3 is configured in such a way that it lets through the exciting radiation but reflects the expected longer-wavelength luminescent radiation.

If the bottle has no contaminants, part of the exciting radiation is reflected back out of the bottle opening and then passes through the dichroic mirror 3 without being deflected on to the CCD camera 5.

If, however, a luminescent contaminant is present in the bottle, i.e. a contaminant that reacts to the exciting radiation with a luminescence phenomenon, part of the luminescent radiation emitted by the contaminant leaves the bottle through the mouth and strikes the dichroic mirror 3. The dichroic mirror 3 reflects this longer-wavelength luminescent radiation on to the CCD camera 5, in which the radiation is then detected.

In addition, a filter 4 can be provided to prevent parts of the exciting radiation from reaching the CCD camera or to allow only certain frequency ranges to pass selectively.

The embodiment illustrated in FIG. 1 is particularly suitable for inspecting containers in which the entire internal space of the container can be illuminated via the container opening, e.g. bottles with long, slowly widening bottle necks or containers with large mouth openings.

Figure 2:
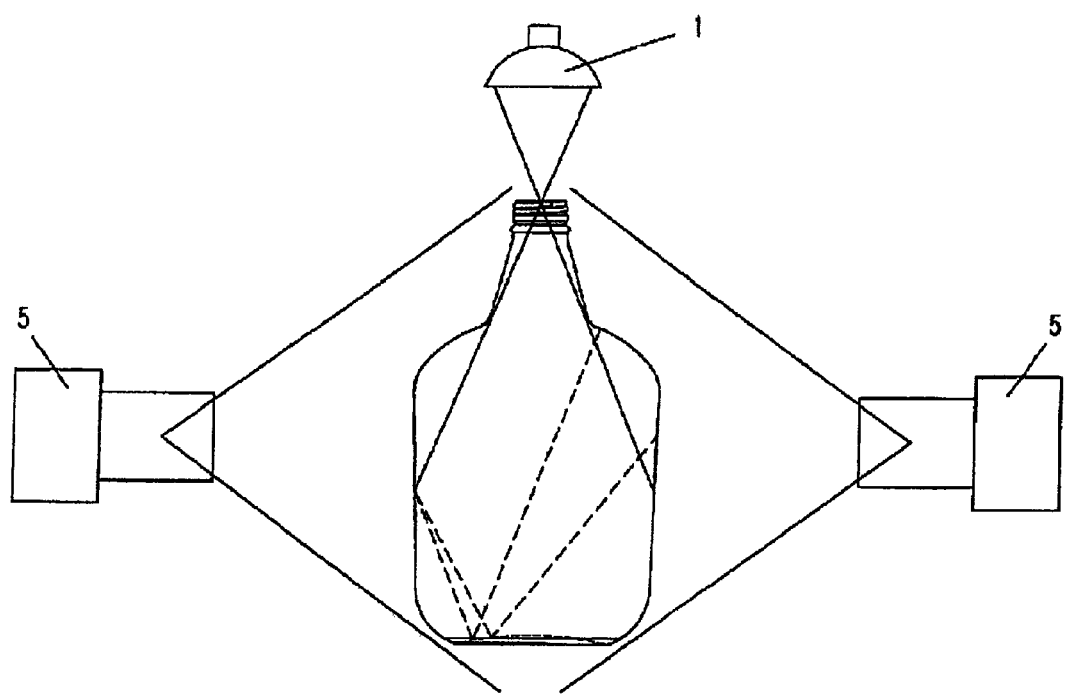
FIG. 2 a pictorial schematic of a second apparatus for inspecting empty containers.

In the case of containers which, owing to their geometry, do not permit illumination of the inner walls via the mouth opening, a modified setup as shown in FIG. 2 is suitable. However, it is a prerequisite here that the container wall must consist of a material that is transparent to luminescent radiation.

In the apparatus according to FIG. 2, the radiation source is likewise positioned over the container to be examined. The exciting radiation is directed into the interior of the container via the mouth opening of the container. As indicated in FIG. 2, the incident radiation is reflected on the inner side walls and base of the container to be examined, so that with this apparatus too, the entire internal space of the container is illuminated.

Figure 3:
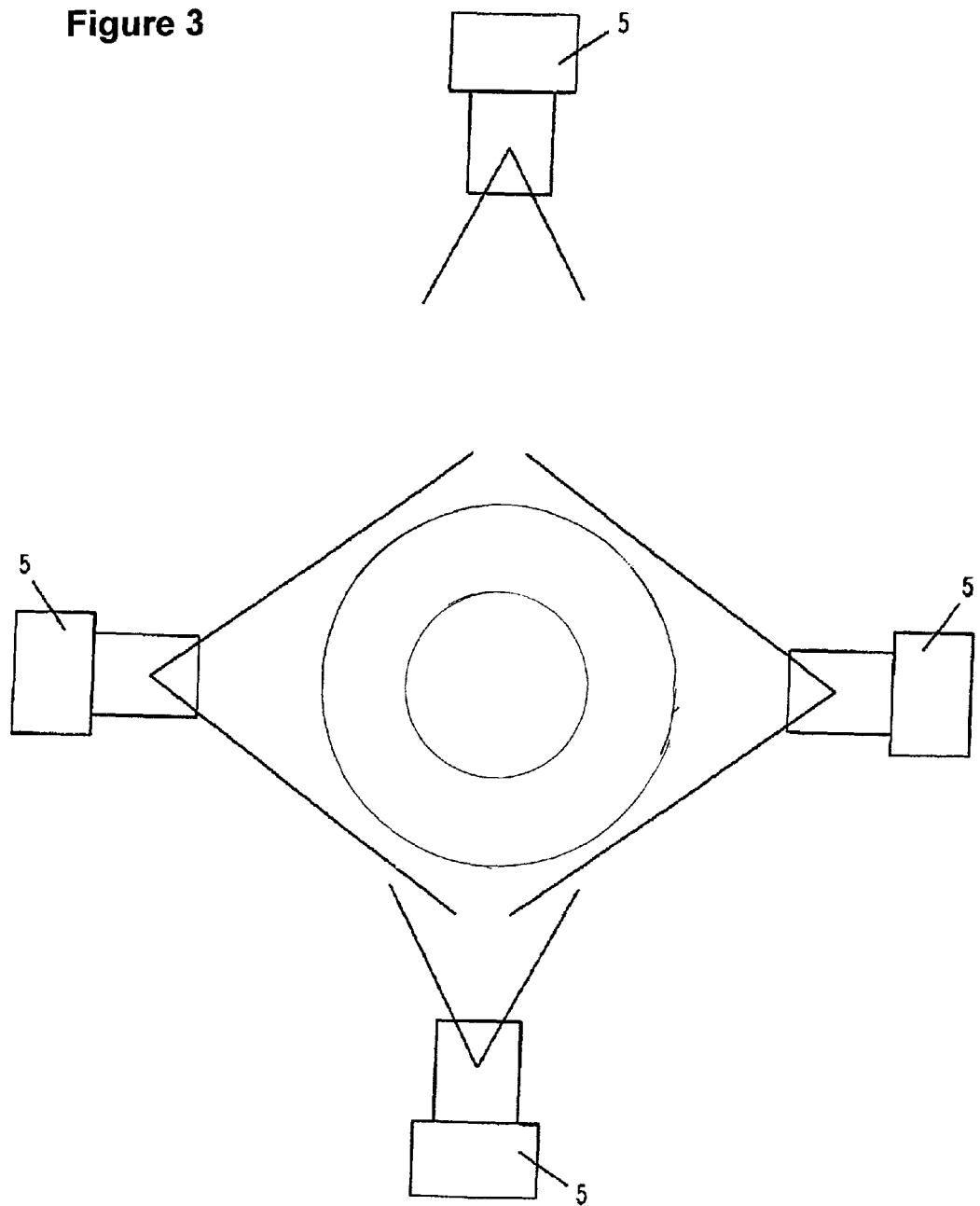
FIG. 3 a top view of the apparatus from FIG. 2.

If, in the apparatus of FIG. 2, there is a luminescent contaminant in the container, this contaminant again emits luminescent radiation as a result of the exciting radiation. As discussed above, the wavelength of the luminescent radiation is greater than that of the exciting radiation and therefore, if the container consists of a material that is transparent to the frequency range of the luminescent radiation, it can also exit the container directly through the container wall. To detect this luminescent radiation, detection devices such as e.g. CCD cameras mounted outside the container are provided. The arrangement of the detection devices is illustrated in the top view of FIG. 3. In this arrangement, sets of 2 CCD cameras are each arranged opposite one another in pairs. The number and arrangement of the detection devices can, however, be selected at will, provided that it is ensured that a complete image of the container is achieved. It is also possible to mount detection devices below or above the containers to be examined.

An additional filter for blocking the exciting radiation is not necessary in this embodiment if the material of the container is non-transparent to the exciting radiation. The embodiment from FIG. 2 is particularly suitable e.g. for examining glass containers by UV radiation. Container glass is typically almost impermeable to UV radiation. The luminescent radiation emitted by contaminants, on the other hand, has a higher wavelength, which is predominantly in the visible range and can therefore pass through the container wall without any problems.

The invention claimed is:

1. Apparatus for inspecting empty containers for contaminants, comprising
   a pulsed radiation source for generating an exciting radiation, wherein the pulsed radiation source is configured such that:
      the exciting radiation is directed on to the inner wall of a container having an internal space,
      the exciting radiation illuminates all of the internal space; and
      the exciting radiation excites contaminants to be detected in such a way that they emit luminescent radiation,
   at least one device for detecting the luminescent radiation emitted by the contaminants, and
   a device for analysing the detected luminescent radiation.

2. Apparatus according to claim 1, wherein the pulsed radiation source comprises an electromagnetic radiation source that emits electromagnetic radiation selected from a group consisting of: visible light, UV-A light, UV-B light, UV-C light, and X-ray radiation.

3. Apparatus according to claim 1, wherein the exciting radiation is directed through the container opening into the interior of the container.

4. Apparatus according to claim 1, wherein the pulsed radiation source is introduced through a container opening into the interior of the container.

5. Apparatus according to claim 1, wherein the luminescent radiation emitted by the contaminants is guided out of the container through the container opening and directed on to the detection device.

6. Apparatus according to claim 5, comprising a dichroic mirror which lets through the exciting radiation and directs the luminescent radiation exiting from the container opening on to the detection device.

7. Apparatus according to claim 1, wherein the luminescent radiation emitted by the contaminants is guided out of the container through the walls of the container and collected by one or more detection devices, which are arranged around the container.

8. Method for inspecting empty containers for contaminants, comprising the steps:
   irradiating the inner walls of a container with an exciting radiation from a pulsed radiation source, wherein
      the container has an internal space and the exciting radiation illuminates all of the internal space, and
      the exciting radiation excites contaminants to be detected in such a way that they emit luminescent radiation;
   detecting the luminescent radiation emitted by the contaminants using a detection device; and
   analysing the detected luminescent radiation in an analysing device.

9. Method according to claim 8, wherein the pulsed radiation source comprises an electromagnetic radiation source that emits electromagnetic radiation selected from a group consisting of: visible light, UV-A light, UV-B light, UV-C light, and X-ray radiation.

10. Method according to claim 8, wherein the exciting radiation is directed through a container opening into the interior of the container.

11. Method according to claim 8, wherein the radiation source is introduced into the interior of the container through a container opening.

12. Method according to claim 8, wherein the radiation source used has at least a proportion of UV-C radiation, so that organic contaminants are detected and at the same time rendered harmless.

13. Method according to claim 8, wherein a contaminated container is rejected only if the detected luminescent radiation exceeds a previously set limit value.

14. Method according to claim 8, wherein the exciting radiation causes the contaminants to phosphoresce and to fluoresce, and the luminescent radiation resulting from the phosphorescence and the fluorescence of the contaminants is analysed.

15. Apparatus for inspecting empty containers for contaminants, comprising
   a radiation source for generating an exciting radiation, wherein the radiation source is configured such that:
      the exciting radiation is directed on to the inner wall of a container having an internal space, the exciting radiation illuminates all of the internal space, and the exciting radiation excites contaminants to be detected in such a way that they emit luminescent radiation, at least one device for detecting the luminescent radiation emitted by the contaminants, and a shutter camera for analysing the detected luminescent radiation.

16. Apparatus according to claim 15, wherein the radiation source comprises an electromagnetic radiation source that emits electromagnetic radiation selected from a group consisting of: visible light, UV-A light, UV-B light, UV-C light, and X-ray radiation.

17. Apparatus according to claim 15, wherein the exciting radiation is directed through the container opening into the interior of the container.

18. Apparatus according to claim 15, wherein the radiation source is introduced through a container opening into the interior of the container.

19. Apparatus according to claim 15, wherein the luminescent radiation emitted by the contaminants is guided out of the container through the container opening and directed on to the detection device.

20. Apparatus according to claim 19, comprising a dichroic mirror which lets through the exciting radiation and directs the luminescent radiation exiting from the container opening on to the detection device.

* * * * *